United States Patent [19]

Bala et al.

[11] Patent Number: 5,369,525
[45] Date of Patent: Nov. 29, 1994

[54] RING LENS ASSEMBLY FOR AN OPTICAL VIEWING DEVICE

[75] Inventors: John Bala, Pomfret, Conn.; Xiaohui Ning, Northboro, Mass.

[73] Assignee: United States Surgical Corporation, Norwalk, Conn.

[21] Appl. No.: 985,686

[22] Filed: Dec. 2, 1992

[51] Int. Cl.$^5$ .............................................. G02B 17/00
[52] U.S. Cl. ................................. 359/435; 359/434; 359/509; 359/819; 385/117
[58] Field of Search ............... 359/434, 435, 367, 509, 359/819; 385/117

[56] References Cited

U.S. PATENT DOCUMENTS

| | | |
|---|---|---|
| 2,245,257 | 6/1941 | Crumrine . |
| 2,266,169 | 12/1941 | Crumrine . |
| 2,304,984 | 12/1942 | Wood . |
| 2,341,364 | 2/1944 | Crumrine . |
| 2,388,893 | 11/1945 | Wood . |
| 2,482,971 | 9/1949 | Golson . |
| 3,089,484 | 5/1963 | Hett . |
| 3,257,902 | 6/1966 | Hopkins . |
| 3,297,022 | 1/1967 | Wallace . |
| 3,414,344 | 12/1968 | McKollma . |
| 3,484,148 | 12/1969 | Gotoh . |
| 3,556,085 | 1/1971 | Takahashi . |
| 3,677,262 | 7/1972 | Zukowski . |
| 3,888,568 | 6/1975 | Norris et al. . |
| 3,941,121 | 3/1976 | Olinger et al. . |
| 4,036,218 | 7/1977 | Yamashita et al. . |
| 4,076,018 | 2/1978 | Heckele . |
| 4,148,550 | 4/1979 | MacAnally . |
| 4,148,551 | 4/1979 | MacAnally . |
| 4,157,216 | 6/1979 | Plummer . |
| 4,159,546 | 7/1979 | Shearing . |
| 4,267,828 | 5/1981 | Matsuo . |
| 4,273,110 | 6/1981 | Groux . |
| 4,319,563 | 3/1982 | Kubota . |
| 4,392,485 | 7/1983 | Hiltebrandt . |
| 4,545,652 | 10/1985 | Hoogland . |
| 4,574,783 | 3/1986 | Kazuhiro et al. . |
| 4,575,195 | 3/1986 | Hoogland . |

(List continued on next page.)

FOREIGN PATENT DOCUMENTS

| | | |
|---|---|---|
| 3534210 | 3/1986 | Germany . |
| 3535028 | 4/1986 | Germany . |
| 544422 | 1/1977 | Russian Federation . |
| 686725 | 4/1979 | Russian Federation . |
| 683721 | 9/1979 | Russian Federation . |
| 8807218 | 9/1988 | WIPO . |
| 9104703 | 4/1991 | WIPO . |

OTHER PUBLICATIONS

Thomas Aquilina, David Richards and Harvey Pollicove, Technology Trends, Sep. 1986, Photonics Spectra.

(List continued on next page.)

Primary Examiner—John T. Kwon

[57] ABSTRACT

A ring lens assembly for an optical viewing device is presented. The ring lens assembly includes a ring shaped lens adapted for mounting at the end of an optical viewing device for viewing a remote location. The optical viewing device comprises an objective lens section, a relay lens section and an eye piece section. Further, the optical viewing device has an inner tube wherein the optics is housed and an outer tube. A plurality of optical fibers are disposed between the inner and outer tubes to provide illumination of the field of view. The ring shaped lens is a negative curvature lens or a prism-like lens for increasing the field of illumination. Alternatively, the lens is a flat lens and the optical fibers twisted to increase the field of illumination. Also, a cleaning tube is disposed between the inner and outer tubes. The cleaning tube terminates short of the end of the inner tube. An opening or channel is formed at the end of the inner tube adjacent to the cleaning tube. Accordingly, cleaning fluid travels down the cleaning tube and impacts the inner surface of the ring shaped lens. The cleaning fluid is deflected off of the inner surface of the ring lens, flows through the opening in the inner tube and impacts the outer surface of the first lens in the objective lens section thereby providing cleaning action.

27 Claims, 4 Drawing Sheets

U.S. PATENT DOCUMENTS

| | | |
|---|---|---|
| 4,608,966 | 9/1986 | Storz . |
| 4,664,486 | 5/1987 | Landre et al. . |
| 4,676,606 | 6/1987 | Takahashi . |
| 4,693,568 | 9/1987 | Takahashi . |
| 4,704,007 | 11/1987 | Landre et al. . |
| 4,765,313 | 8/1988 | Kamakura . |
| 4,784,118 | 11/1988 | Fantone et al. . |
| 4,802,460 | 2/1989 | Ohkuwa et al. . |
| 4,822,154 | 4/1989 | Oxford et al. ................. 359/435 |
| 4,869,238 | 9/1989 | Opie et al. . |
| 4,878,485 | 11/1989 | Adair . |
| 4,919,112 | 4/1990 | Siegmund . |
| 4,946,267 | 8/1990 | Hoogland . |
| 4,964,710 | 10/1990 | Leiner . |
| 4,993,817 | 2/1991 | Hoogland . |
| 5,046,816 | 9/1991 | Lehmann et al. . |
| 5,059,009 | 10/1991 | McKinley . |

OTHER PUBLICATIONS

Harvey Pollicove and Thomas Aquilina, Injection Mounting, Dec. 1987, Photonics Spectra.

John D. Lytle, Specifying Glass and Plastic Optics—What's The Difference? 1979, SPIE vol. 181 Contemporary Optical Systems & Components Specifications.

Harold H. Hopkins, Optical Principles of the Endoscope, 1976.

RING LENS ASSEMBLY FOR AN OPTICAL VIEWING DEVICE

BACKGROUND OF THE INVENTION

This invention relates generally to optical viewing devices. More particularly, this invention relates to a ring lens assembly for an optical viewing device for viewing remote locations which are difficult or impossible to directly access.

Optical viewing devices of the type described herein are well known and used in a variety of applications. For example, such devices are configured as borescopes and used to view or inspect the interior of remote cavities such as engine cylinders and the like. Borescopes thus find extensive utility in the automotive and aerospace industries. In the medical field, such optical viewing devices are configured as endoscopes or laparoscopes. Endoscopes (or laparoscopes) are well known medical instruments which are used to visualize the interior of a body cavity or hollow organ. Endoscopes are used in a variety of operative procedures including laparoscopic surgery where endoscopes are used to visually examine the peritoneal cavity.

Typical prior art optical viewing devices (e.g., borescopes and endoscopes) comprise three main sections including an objective lens followed by a relay lens followed by an eye piece. The relay lens section functions to transmit the image rays obtained by the objective lens along a preselected distance to the eye piece. The relay lens may consist of either a coherent fiber optical bundle or a series of lenses. When the relay lens section is comprised of a series of lenses, the lens series traditionally includes repeated units (e.g., three) with each unit comprising a symmetric arrangement of glass rods and lens groupings. Thus, in a prior art device having three relay sections, a total of six glass rods and associated lens groupings were required. These glass rods are used to preclude or lessen divergence of the image rays as they travel through the optical viewing device. Such glass rods must be of a high optical quality and therefore the glass rods lead to a relatively high manufacturing cost for each optical viewing device. Moreover, in certain prior art viewing devices, the objective lens and eye piece sections also contain glass rods leading to even higher manufacturing costs.

Illumination in the remote location to be viewed is required. A preferred method of transmitting illumination light is to use a bundle of optical fibers surrounding the outer circumference of the optical viewing device. These fibers are generally glass. The field of illumination should be of a size no less than the field of view (FOV) of the optical viewing device. Typically, the FOV may range between 30 to 75 degrees.

The method of illuminating the remote location to be viewed in both U.S. patent application Ser. No. 838,602 filed Feb. 19, 1992 assigned to the assignee hereof and incorporated herein by reference and in U.S. patent application Ser. No. 944,212 filed Sep. 11, 1992 assigned to the assignee hereof and incorporated herein by reference is accomplished by using the low cost plastic optical fibers. However, because plastic optical fibers have a relatively small numerical aperture and thus, a small field of illumination, the fibers are twisted (e.g., 15 degrees), the field of illumination is increased and may be tailored to match (or be no less than) the size of the field of view of the optical viewing device.

The devices of U.S. Ser. Nos. 838,602 and 944,212 further include a cleaning tube longitudinally along the length of the optical viewing the device. The cleaning tube is connected to a valve at one end thereof for injecting a cleaning fluid and protrudes outwardly from the other end thereof. The protruding end of the cleaning tube may inadvertently puncture or otherwise damage tissue within a body cavity when the device is used as an endoscope or a laparoscope.

SUMMARY OF THE INVENTION

The above-discussed and other problems and deficiencies of the prior art are overcome or alleviated by the ring lens assembly for an optical viewing device of the present invention. In accordance with the present invention, a ring lens assembly for an optical viewing device is presented. The ring lens assembly includes a ring shaped lens adapted for mounting at the end of an optical viewing device for viewing a remote location. The optical viewing device comprises an objective lens section, a relay lens section and an eye piece section. Further, the optical viewing device has an inner tube wherein the optics is housed and an outer tube. A plurality of optical fibers (preferably plastic optical fibers) are disposed between the inner and outer tubes to provide illumination of the field of view. These optical fibers terminated at the ring shaped lens which is disposed within the outer tube. The ring shaped lens may be a negative curvature lens or prism-like lens for increasing the field of illumination. Alternatively the lens may be a flat lens and the optical fibers twisted to increase the field of illumination. Also, a cleaning tube is disposed between the inner and outer tubes. The cleaning tube terminates short of the end of the inner tube. An opening or channel is formed at the end of the inner tube adjacent to the cleaning tube. Accordingly, cleaning fluid travels down the cleaning tube and impacts the inner surface of the ring shaped lens. The cleaning fluid is deflected off of the inner surface of the ring lens, flows through the opening in the inner tube and impacts the outer surface of the first lens in the objective lens section thereby providing cleaning action.

An important feature of the present invention is the additional cost savings over the prior art in allowing the use of plastic optical fibers without requiring the twisting of the fibers and the cleaning tube to achieve a field of illumination to match (or be no less than) the size of the field of view of the optical viewing device. This is achieved by the use of the negative curvature ring shaped lens.

Further, in a preferred embodiment of the present invention the above defined characteristic of the ring lens are incorporated into the outer lens of the object lens portion of the viewing device.

Another important feature of the present invention is the elimination of the protruding end of the cleaning tube. The cleaning tube of the present invention provides the same cleaning action as the prior art devices without the risk of puncturing or otherwise damaging tissue in a body cavity when the device is used as an endoscope or a laparoscope.

BRIEF DESCRIPTION OF THE DRAWINGS

Referring now to the drawings, wherein like elements are numbered alike in the several FIGURES.

DESCRIPTION OF THE PREFERRED EMBODIMENT

Figure 1:
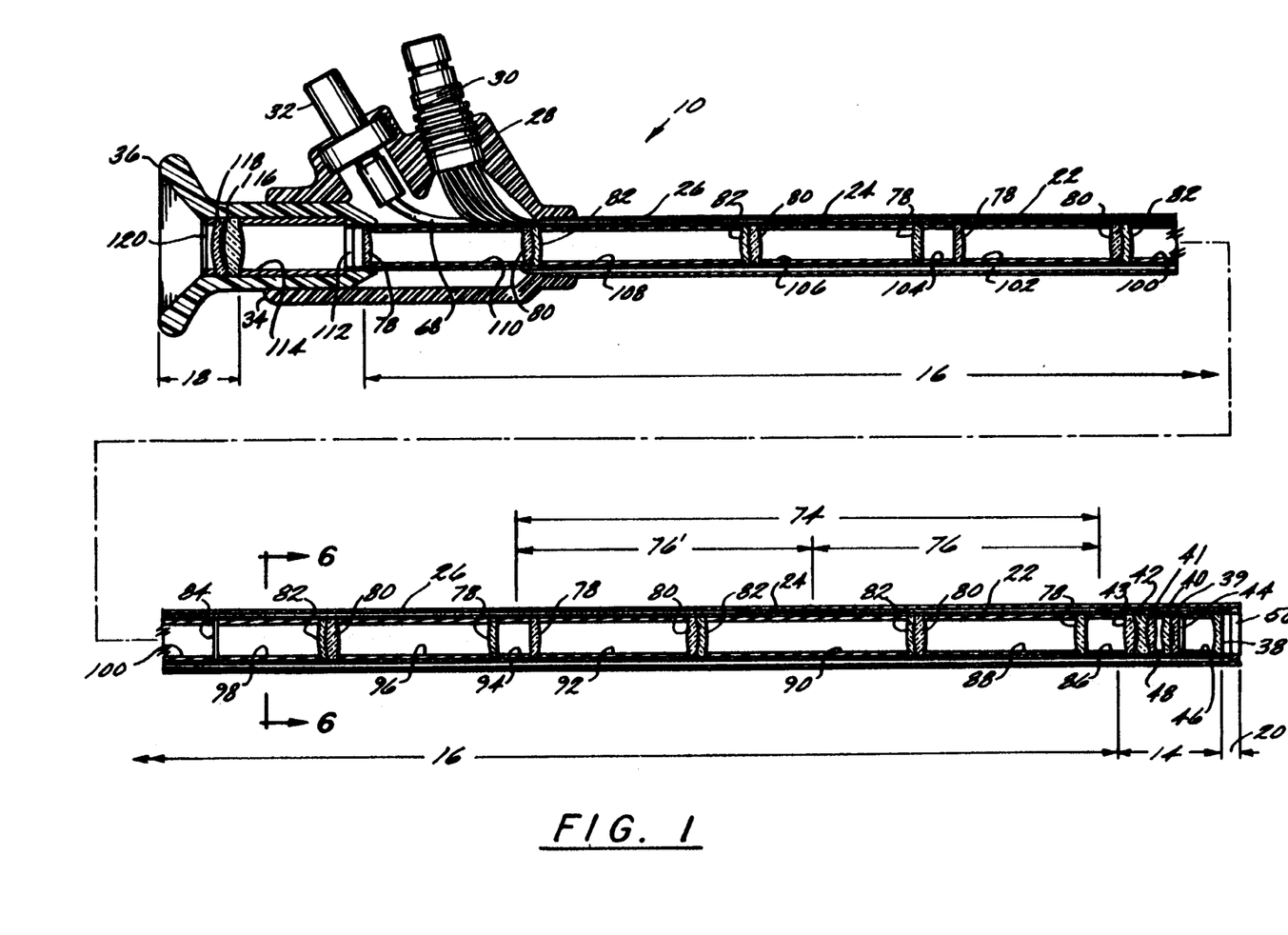
FIG. 1 is a side elevational view, partly in cross-section, of an optical viewing device employing the ring lens assembly in accordance with the present invention.

Referring now to FIG. 1, an optical viewing device employing a ring lens assembly in accordance with the present invention is shown generally at 10. Device 10 comprises an optical viewing device 12 having three main sections including an objective lens section 14, a relay lens section 16 and an eye piece lens section 18, and a ring lens assembly 20. By way of example, the optical viewing device 12 shown in FIG. 1 is the optical viewing device of U.S. Ser. No. 944,212 which includes six lenses in the objective lens section 14, eighteen lenses in the relay lens section 16 and two lenses in the eye piece lens section 18 for a total of twenty-six lenses. In general, these lenses are spaced apart by air gaps and are retained in place by a series of spacer sleeves. The series of lenses and spacer sleeves are positioned within an inner tube 22. Surrounding inner tube 22 is a plurality of optical fibers 24. Optical fibers 24 are sandwiched between inner tube 22 and an outer tube 26. Preferably, both inner tube 22 and an outer tube 26 are comprised of a stainless steel. Both inner and outer tubes 22 and 26 terminate at a body housing 28 which houses a fiber optic connector 30 and a cleaning fluid injection port 32. In turn, body housing 28 includes an opening 34 for receiving an eye piece housing 36. It will be appreciated that optical viewing device 12 may also be of the type described in U.S. Ser. No. 838,602 or any other optical viewing device having inner and outer tubes with the optics houses within the inner tube, the optics including an objective lens section, a relay lens section and an eye piece section.

Figure 2:
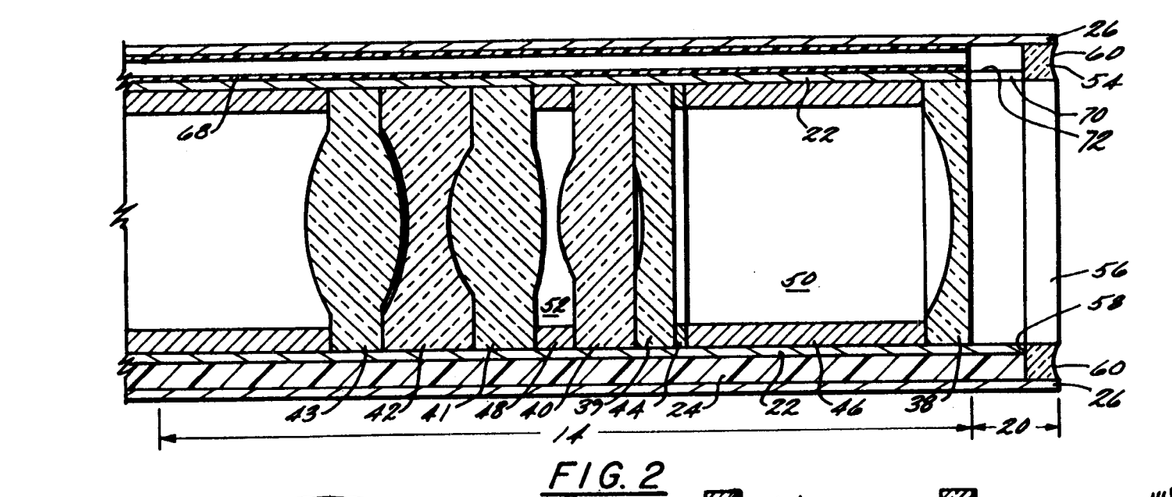
FIG. 2 is an enlarged cross-sectional elevational view of the end of the optical viewing device employing the ring lens assembly of FIG. 1.
Figure 3:
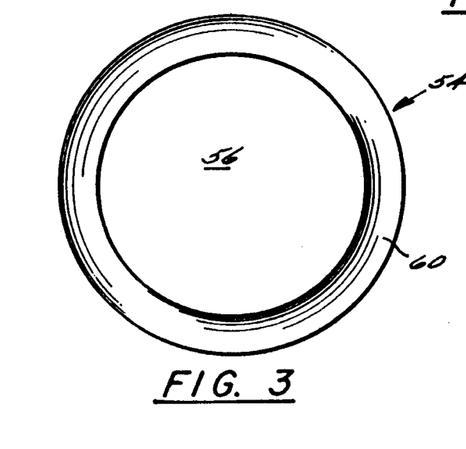
FIG. 3 is an enlarged end view of the ring lens employed in FIG. 1.

Also referring to FIGS. 2 and 3, the objective lens section 14 comprises six lenses including lenses 38–43. It will be appreciated that the physical and optical characteristics of each of the lenses 38–43 for objective lens section 14 (as well as relay lens section 16 and eye piece lens section 18) are the same as set forth in Table 1 of U.S. Ser. No. 944,212.

Ring lens assembly 20 comprises a ring shaped lens (i.e., an annular lens) 54 having a central opening 56 which aligns with lens 38 of the objective lens section 14. Unlike lenses 38–43, lens 54 may be mounted within the outer tube 26 with inner tube 22 abutting an inner flat surface 58 of lens 54. Alternatively, lens 54 could be secured (e.g., by a suitable epoxy) to the fibers 24 and the inner and outer tubes 22, 26.

Since the optical viewing device of the present invention is typically used to view remote locations which may have little or no illumination, the present invention includes a means for illuminating the remote end (the end to the right of the objective lens section) so that light from this illuminating means may be reflected from the object to be viewed and thereafter travel through device 10 as described in U.S. Ser. No. 944,212. In a preferred embodiment, the illuminating means comprise a plurality of optical fibers which are arranged in one or more layers along the inner circumference of outer tube 26. Optical fibers 24 are collected in a bundle in body housing 28 and attached to a commercially available and known fiber optic connector 30. In a known manner, a light source is positioned at the terminal end of connector 30 to provide light to the fiber optic bundle. In this way, light is provided to the field of view of the objective lens section for purposes of illumination.

The optical fibers 24 are comprised of a suitable polymeric material such as acrylic or polycarbonate materials. The use of polymeric optical fibers results in lower cost and more light weight relative to prior art glass fiber materials. However, one problem with polymeric optical fibers is that the field of illumination is relatively small because of their small numerical aperture (as compared to glass fibers) and may therefore not be as large as desired (which is typically a field of illumination at least equal to the FOV of the device 10).

However, this problem has been overcome by lens 54, which has a front surface comprising a negative curvature 60. The fibers 24 align with the negative curvature 60 and are optically coupled with and physically attached to surface 58 of lens 56 by any well known means (e.g., by a suitable epoxy). Lens 54 is preferably a plastic lens comprised of a suitable optical grade plastic (e.g., a polymeric material). However, it is within the scope of the present invention that lens 54 be comprised of a optical grade glass. The negative curvature 60 increases the field of illumination to obtain a field of illumination which is at least equal to the desired field of view for the device 10. The negative curvature 60 eliminates the need to twist the fibers as is taught in U.S. Ser. Nos. 838,602 and 944,212.

Figure 4:
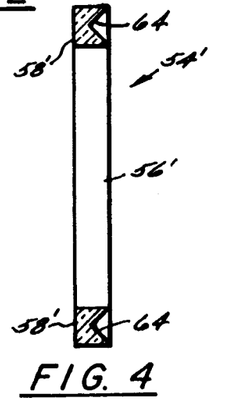
FIG. 4 is an enlarged cross-sectional side elevational view of a ring lens for an optical viewing device in accordance with an alternate embodiment of the present invention.

Referring to FIG. 4, in another embodiment, the ring shaped lens employs the lens design shown generally at 54'. Lens 54' has a front surface comprising a double angled or wedge shape 64, a flat rear surface 58' and a central opening 56'. Similar to the negative curvature 60 (FIG. 2) the wedge shape 64 of lens 54' increases the field of illumination to obtain a field of illumination which is at least equal to the desired field of view for the device 10.

Figure 5A:
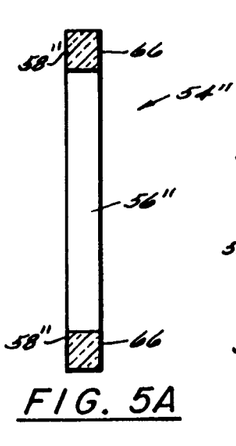
FIG. 5A is an enlarged cross-sectional side elevational view of a ring lens for an optical viewing device in accordance with still another alternate embodiment of the present invention.
Figure 6:
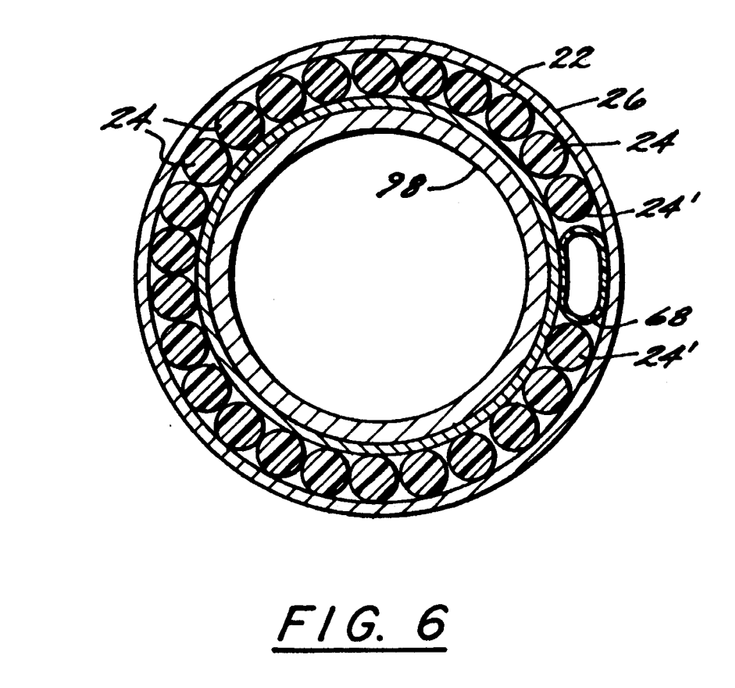
FIG. 6 is a cross-sectional elevational view along the line 6—6 of FIG. 1.

Referring to FIG. 5A, in still another embodiment, the ring shaped lens employs the lens design shown generally at 54''. Lens 54'' has a flat front surface 66, a flat rear surface 58'' and a central opening 56''. However, with lens 54'' the polymeric optical fibers 24 are twisted as is described in U.S. Ser. Nos. 838,602 and 944,212. Such twisting significantly increase the field of illumination to obtain a field of illumination which is equal to the desired field of view for the device 10. Preferably, the optical viewing device 10 of the present invention utilizes twenty-five one millimeter diameter acrylic fibers 24 as shown in FIG. 6. Also, in this embodiment the fibers for the reasons mentioned above are twisted to an angle in the range of between 10° and 15°.

Figure 5B:
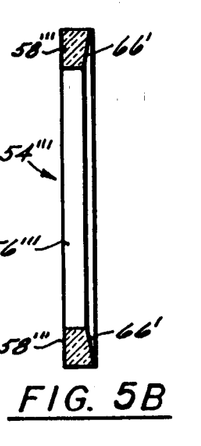
FIG. 5B is an enlarged cross-sectional side elevational view of a ring lens for an optical viewing device in accordance with still yet another alternate embodiment of the present invention.

Referring to FIG. 5B, is still yet another embodiment, the ring shaped lens employs the lens design shown generally at 54'''. Lens 54''' has an angled or prism-like shape 66', a flat rear surface 58''' and a central opening 56'''. Similar to the negative curvature 60 (FIG. 2) the angled shape 66' of lens 54''' increases the field of illumination to obtain a field of illumination which is at least equal to the desired field of view for the device 10.

Figure 7:
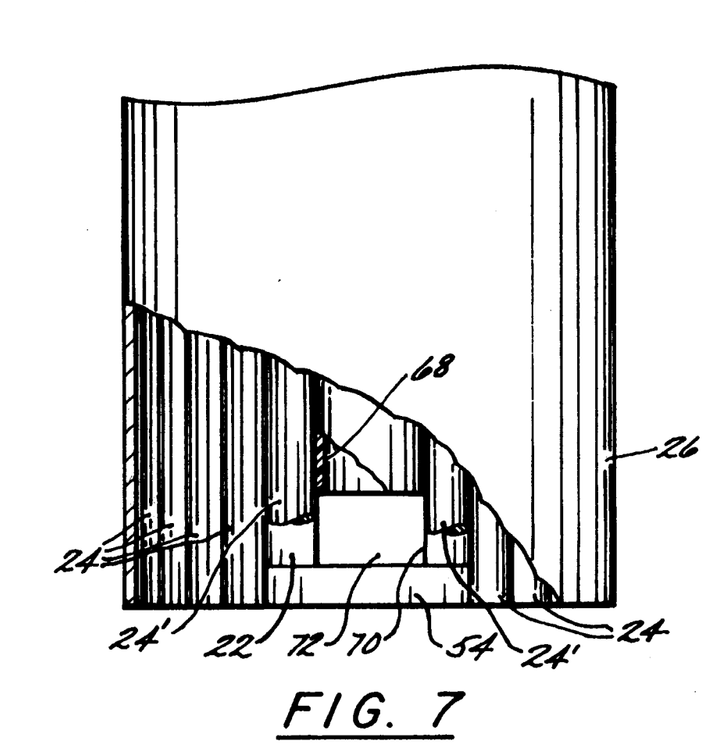
FIG. 7 is an enlarged top partially cut away view of the the end of the optical viewing device employing the ring lens assembly of FIG. 1.

In certain applications, it may be desirable to provide a means for maintaining the outer surface of lens 38 (the first lens in objective lens section 14) clean and free of any obscurations. If such a cleaning means is desired, the present invention employs valve 32 received in an appropriate opening in housing 28. Valve 32 is connected to a plastic tube 68 which runs longitudinally along the length of inner tube 22 and is sandwiched between a pair of optical fibers 24' as best shown in FIG. 6. Inner tube 22 has an opening or channel 70 (FIG. 7) at an end 72 thereof. Tube 68 terminates at opening 70 and is aligned therewith. Accordingly, an opening 74 is defined between the end of tube 68 and surface 58 of lens 54. Thus, when it is desired to clean lens 38, a suitable cleaning fluid is injected through valve 32, travels down through tube 68 and impacts surface 58 of lens 54. The cleaning fluid is deflected off of surface 58, flows through opening 70 in the inner tube 22 and impacts the outer surface of lens 38 thereby providing cleaning action.

Relay lens section 16 comprises eighteen lenses. These eighteen lenses are arranged in three repeating units, each repeating unit comprising two symmetrical sub-units of three unique lenses. One such repeating unit is shown in FIG. 1 and identified at 74. As mentioned, repeating unit 74 includes two symmetrical sub-units 76 and 76'. In turn, each sub-unit 76, 76' each include three unique lenses 78, 80 and 82. It will be appreciated that the lens arrangement 76' is a mirror image of the lens arrangement 76.

Eye piece housing 36 houses the eye piece lens section 18 and a field stop 112. Field stop 112 (i.e., an annular disk) is preferably comprised of stainless steel and functions to define the field of view (FOV) of the optical system. Field stop 112 and eye piece lens section 18 are separated by a spacer sleeve 114 of the type described hereinabove with an air space residing within spacer sleeve 114. Eye piece lens section 18 comprises two lenses 116 and 118, each having outer flange sections which abut one another but provide a small air space therebetween.

Housing body 28 (as well as eye piece housing 36) are preferably comprised of a molded plastic.

Figure 8:
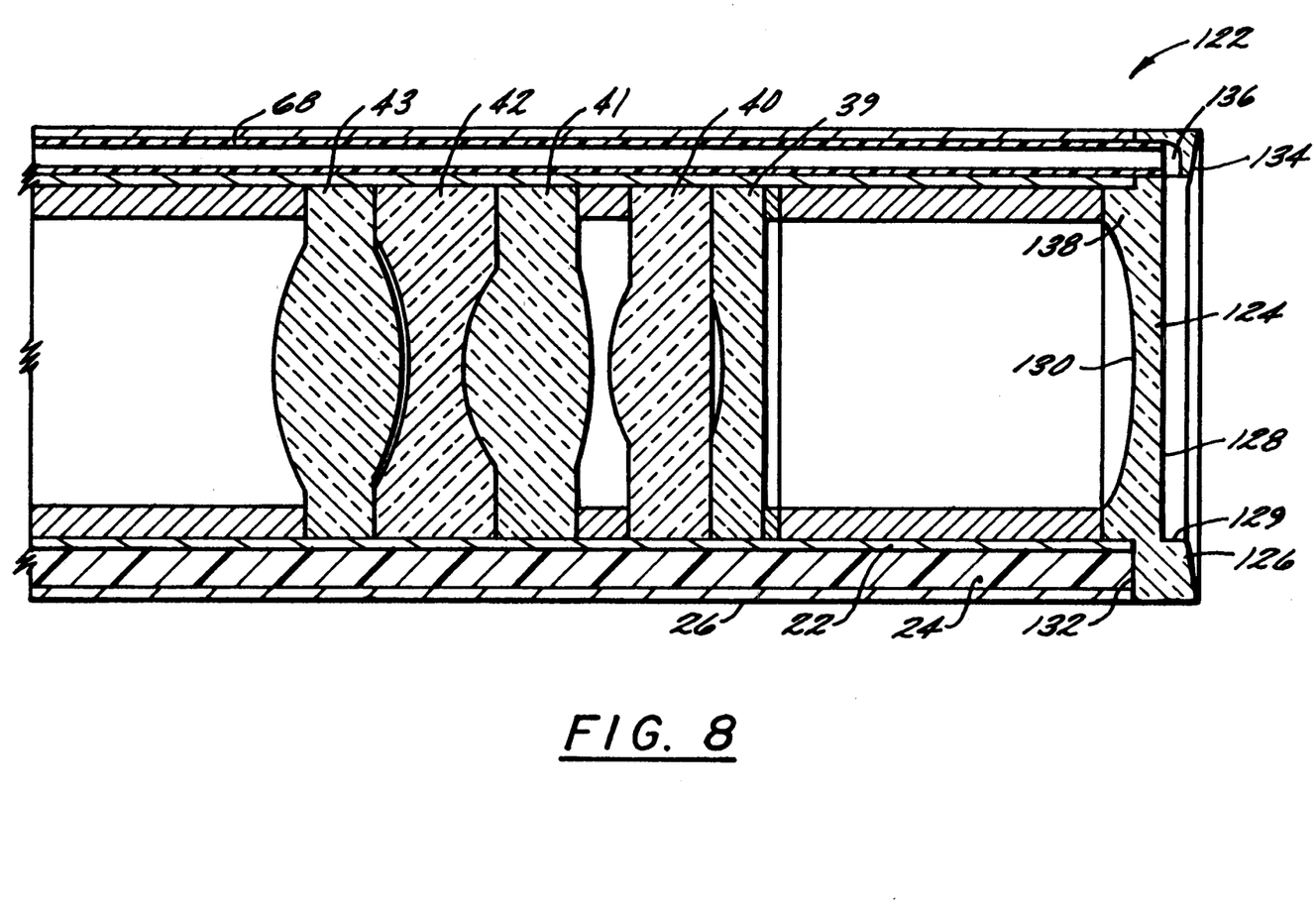
FIG. 8 is an enlarged cross-sectional elevational view of the end of an optical viewing device in accordance with a preferred embodiment of the present invention.

Referring to FIG. 8, a preferred embodiment of the optical viewing device of the present invention is shown generally at 122. Device 122 is the same as device 10 of the embodiment of FIGS. 1 and 2 herein with the exception that the lenses 38 and 54 (i.e., ring lens assembly 20) of the embodiment of FIGS. 1 and 2 have been replaced by a lens 124. Accordingly like elements between these embodiments are numbered alike.

Lens 124 may be plastic and comprised of any suitable optical polymeric material, preferably polymethylmethacrylate, polystyrene and polycarbonate. While lens 124 has been described as a plastic lens, it is within the scope of the present invention that lens 124 be comprised of a optical grade glass.

Lens 124 includes a raised outer circumferential partial 126 defining a recessed portion 128 (i.e., a flat lens surface) and a wall 129 therebetween. Opposite surface 128 is a negative curvature surface 130. The outer portion 126 includes an angled or tilted surface 134.

The fibers 24 align with the angled surface 134 and are optically coupled with and physically attached to surface 132 of lens 124 by any well known means (e.g., by a suitable epoxy). The tilt or angle of surface 134 increases the field of illumination to obtain a field of illumination which is at least equal to the desired field of view for the device 122. The tilt and angle of surface 134 eliminates the need to twist the fibers as is taught in U.S. Ser. Nos. 838,602 and 944,212.

Again the cleaning means of the present invention employs valve 32 received in an appropriate opening in housing 28. Valve 32 is connected to plastic tube 68 which runs longitudinally along the length of inner tube 22 and is sandwiched between a pair of optical fibers 24'.

Lens 124 includes an opening or channel 136 therethrough which extends from surface 132 to wall 129. Tube 68 terminates in channel 136. Thus, when it is desired to clean surface 128, a suitable cleaning fluid is injected through valve 32, travels down through tube 68, into and through channel 136 of lens 124 and impacts surface 128 of lens 124, thereby providing cleaning action.

Lens 124 is secured to the ends of tubes 22 and 26 and fibers 24 at surface 132 by a suitable epoxy. Lens 124 is further secured within inner tube 22 by projecting portions 138.

The present invention thus provides a relatively low cost and light weight optical viewing device which finds utility both as an endoscope and as a borescope and in any other application wherein a remote object positioned in cavity or the like must be viewed. It will be appreciated that the cost of the viewing device of the present invention, as with the optical viewing devices of U.S. Ser. Nos 838,602 and 944,212, may be so low that in certain applications, the present invention may be a disposable item. The need for disposable viewing devices of the type described herein is particularly important in the medical field where infection and other contamination is an important consideration in medical instrumentation and therefore disposable devices are preferred.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An optical viewing device comprising:
   an outer tubular housing having opposed first and second ends;
   an inner tubular housing disposed within said outer tubular housing and having opposed first and second ends, said inner tubular housing having an eye piece section adjacent said first end thereof, a relay lens section adjacent said eye piece section and an objective lens section adjacent said relay lens section wherein said relay lens section is disposed between said eye piece section and said objective lens section;

illuminating means disposed within an annular space defined between said inner and outer tubular housings, said illuminating means defining a predetermined field of illumination; and a ring lens disposed at a light emitting end of said illuminating means and in general alignment therewith, said ring lens having at least one lens surface to increase the predetermined field of illumination defined by said illuminating means.

2. The device of claim 1 wherein said illuminating means comprises a plurality of optical fibers circumferentially disposed within said annular space defined between said inner and outer tubular housings.

3. The device of claim 2 wherein said optical fibers are comprised of a polymeric material.

4. The device of claim 1 wherein said ring lens comprises a material selected from the group consisting of optical plastic and optical glass.

5. The device of claim 1 wherein said ring lens includes a negative curvature surface.

6. The device of claim 1 wherein said ring lens includes a wedge shaped surface.

7. The device of claim 1 further comprising cleaning means for dispensing cleaning fluid against an outer surface of said objective lens arrangement.

8. An endoscope comprising:
an outer tube defining a longitudinal axis;
an inner tube concentrically mounted within said outer tube;
an optical system disposed within said inner tube for conveying an image of an object, said optical system including an objective lens arrangement disposed at one end of said inner tube;
an illumination system for conveying illuminating light, said illumination system including a plurality of illuminating optical fibers circumferentially disposed within an annular space defined between said inner and outer tubes and defining a predetermined field of illumination; and
a ring lens disposed adjacent light emitting portions of said optical fibers and in substantial longitudinal alignment therewith, said ring lens increasing the field of illumination defined by said illumination system.

9. The endoscope of claim 8 wherein said light emitting end portions of said optical fibers are angularly offset relative to said longitudinal axis of said outer tubular housing.

10. The endoscope of claim 9 wherein said light emitting end portions are angularly offset relative to said longitudinal axis by an angle ranging from about 10 to 15 degrees.

11. An endoscope comprising:
an outer tube defining a longitudinal axis;
an inner tube concentrically mounted within said outer tube;
an illumination system for distally transferring illuminating light, said illumination system including a plurality of optical fibers circumferentially disposed within an annular space defined between inner and outer tubes and defining a predetermined field of illumination;
an optical system disposed within said inner tube for conveying an image of an object, said optical system including an objective lens arrangement disposed at one end of said inner tube; and
a cover lens disposed at one end of said outer tube, said cover lens defining an interior portion in general longitudinal alignment with said objective lens arrangement and a circumferential portion in general longitudinal alignment with said optical fibers, said circumferential portion having at least one surface portion dimensioned to increase the predetermined field of illumination.

12. The endoscope of claim 11 wherein said interior portion of said cover lens includes at least one curved surface and wherein said interior portion is a component of said objective lens arrangement.

13. The endoscope of claim 11 further comprising cleaning means for directing cleaning fluid over an outer surface of said cover lens.

14. The endoscope of claim 13 wherein said cleaning means includes a conduit member longitudinally disposed within said annular space defined between said inner and outer tubes.

15. The endoscope of claim 14 wherein said interior portion of said cover lens is disposed proximal of said circumferential portion of said cover lens and wherein said circumferential portion includes a channel, said channel in communication with said conduit member of said cleaning means and defining a passageway between said conduit member and an outer surface of said interior portion such that cleaning fluid emitted by said conduit member is directed against said outer surface of said interior portion.

16. The endoscope of claim 15 wherein said channel is dimensioned to accommodate an end portion of said conduit member.

17. The endoscope of claim 11 wherein said interior portion of said cover lens is disposed proximal of said circumferential portion.

18. The endoscope of claim 11 wherein said cover lens comprises plastic or glass.

19. The endoscope of claim 11 wherein said at least one surface portion of said circumferential portion of said cover lens defines a negative curvature.

20. The endoscope of claim 11 wherein said at least one surface portion of said circumferential portion of said cover lens includes an angled surface.

21. An endoscope comprising:
an outer tubular housing defining a longitudinal axis;
an inner tubular housing concentrically disposed within said outer tubular housing;
an optical system disposed within said inner tubular housing for transferring an image of an object, said optical system including an objective lens arrangement having a lens component adjacent one end of said outer tubular housing;
a plurality of illuminating optical fibers circumferentially disposed within an annular space defined between said inner and outer tubular housings;
a fluid conduit extending longitudinally within said annular space defined between said inner and outer tubular housings and terminating at a position adjacent said one end of said outer tubular housing; and
a ring lens positioned at said one end of said outer tubular housing in substantial alignment with said optical fibers, said ring lens directing cleaning fluid emitted by said fluid conduit onto an outer lens surface of said lens component of said objective lens arrangement.

22. The endoscope of claim 21 wherein said ring lens has first and second opposing flat surfaces.

23. The endoscope of claim 21 wherein said inner tubular housing has a transverse opening adjacent said outer lens surface of said lens component, said transverse opening providing fluid connection between said fluid conduit and said outer lens surface of said lens component such that cleaning fluid emitted by said fluid conduit impacts said outer lens surface.

24. The endoscope of claim 21 wherein said ring lens has at least one surface dimensioned to increase a field of illumination defined by said optical fibers.

25. A borescope comprising:
a frame member; and
a borescope portion extending distally from said frame member and defining a longitudinal axis, said borescope portion including:
   an outer tube member having proximal and distal end portions;
   an inner tube member concentrically mounted within said outer tube member and having proximal and distal end portions;
   an optical system disposed within said inner tube member for conveying an image of an object, said optical system including an objective lens arrangement disposed at said distal end portion of said inner tube member;
   an illumination system for conveying illuminating light, said illumination system including a plurality of illuminating optical fibers circumferentially disposed within an annular space defined between said inner and outer tubular members and defining a predetermined angular field of illumination; and
   an annular lens member disposed adjacent light emitting end portions of said optical fibers and in general alignment therewith, said annular lens member increasing the angular field of illumination defined by said illumination system.

26. A borescope comprising:
a frame member; and
a borescope portion extending distally from said frame member and defining a longitudinal axis, said borescope portion including:
   an outer tube member having proximal and distal end portions;
   an inner tube member concentrically mounted within said outer tube member and having proximal and distal end portions;
   an illumination system for distally transferring illuminating light, said illumination system including a plurality of optical fibers circumferentially disposed within an annular space defined between said inner and outer tubular members and defining a predetermined angular field of illumination;
   an optical system disposed within said inner tube member for conveying an image of an object; and
   a distal most cover lens disposed at said distal end portion of said borescope portion, said cover lens defining an interior portion in general longitudinal alignment with said objective lens arrangement and a circumferential portion in general longitudinal alignment with said optical fibers, said circumferential portion having at least one surface portion dimensioned to increase the predetermined angular field of illumination.

27. A borescope comprising:
a frame member;
a borescope portion extending distally from said frame member and defining a longitudinal axis, said borescope portion including:
   an outer tubular member having proximal and distal ends;
   an inner tubular member concentrically disposed within said outer tubular member and having proximal and distal ends;
   an optical system disposed within said inner tubular member for transferring an image of an object, said optical system including an objective lens arrangement having a distalmost lens component, said distalmost lens component disposed proximal of said distal end of said outer tubular member;
   illumination means including a plurality of optical fibers circumferentially disposed within an annular space defined between said inner and outer tubular members;
   cleaning means for providing cleaning fluid to clean an outer lens surface of said distalmost lens component of said objective lens arrangement, said cleaning means including a fluid conduit extending longitudinally within said annular space defined between said inner and outer tubular members and terminating at a position proximal said second end of said outer tubular member;
   an annular lens element disposed within said annular space defined between said inner and outer tubular members and positioned at said second end of said outer tubular member; and
   means contained within said borescope portion for directing cleaning fluid emitted by said fluid conduit of said cleaning means onto said outer lens surface of said distalmost lens component of said objective lens arrangement.

* * * * *